United States Patent [19]

Root et al.

[11] Patent Number: 4,948,564

[45] Date of Patent: Aug. 14, 1990

[54] MULTI-WELL FILTER STRIP AND COMPOSITE ASSEMBLIES

[75] Inventors: David Root, Lexington, Mass.; George Lyman, Kennebunk, Me.

[73] Assignee: Costar Corporation, Cambridge, Mass.

[21] Appl. No.: 430,812

[22] Filed: Nov. 2, 1989

Related U.S. Application Data

[60] Division of Ser. No. 187,083, Apr. 28, 1988, Pat. No. 4,895,706, which is a continuation-in-part of Ser. No. 923,906, Oct. 28, 1986, abandoned.

[51] Int. Cl.$^5$ .......................... B01L 3/00; G01N 1/18
[52] U.S. Cl. ..................... 422/101; 422/58; 422/69; 422/102; 422/104; 436/165; 436/178; 436/809
[58] Field of Search ................... 422/102, 99, 101, 58, 422/69, 104; 436/165, 177, 178, 808, 809; 356/244, 246

[56] References Cited

U.S. PATENT DOCUMENTS

| | | | |
|---|---|---|---|
| 4,154,795 | 5/1979 | Thorne | 422/102 X |
| 4,246,339 | 1/1981 | Cole et al. | 422/101 X |
| 4,304,865 | 12/1981 | O'Brien et al. | 422/101 X |
| 4,407,943 | 10/1983 | Cole et al. | 435/180 X |
| 4,427,415 | 1/1984 | Cleveland | 422/101 X |
| 4,493,815 | 1/1985 | Fernwood et al. | 422/101 |
| 4,526,690 | 7/1985 | Kiovsky et al. | 210/335 |
| 4,642,220 | 2/1987 | Björkman | 436/809 X |
| 4,734,192 | 3/1988 | Champion et al. | 422/101 X |
| 4,777,021 | 10/1988 | Wertz et al. | 422/101 |

FOREIGN PATENT DOCUMENTS 8402775 7/1984 World Int. Prop. O. .......... 356/246

*Primary Examiner*—Robert J. Warden
*Assistant Examiner*—Lynn M. Kummert
*Attorney, Agent, or Firm*—Wolf, Greenfield & Sacks

[57] ABSTRACT

A filter strip and composite assemblies for filtering microliter quantities of fluids. A linear array of wells having open top and bottom ends are connected by frangible webs in spaced-apart relation with discrete filter membranes closing the bottom ends of each well. Tabs are provided on the ends of the filter strip for holding the same and supporting the strip in a rectangular holder having alpha-numeric designations for identifying each well in a plurality of such filter strips contained within the holder. The filter strip may be used in a vacuum manifold for applying a pressure differential across the filter membrane and directing the filtrate into an aligned aperture of a closed bottom well of an array of wells held within the manifold. Alternatively, the filter strip may be used with a transfer plate for directing the filtrate from each well of the filter strip to an aligned well of a closed bottom array of wells. Another composite assembly includes a pressure manifold for applying an increased pressure above the membranes.

9 Claims, 5 Drawing Sheets

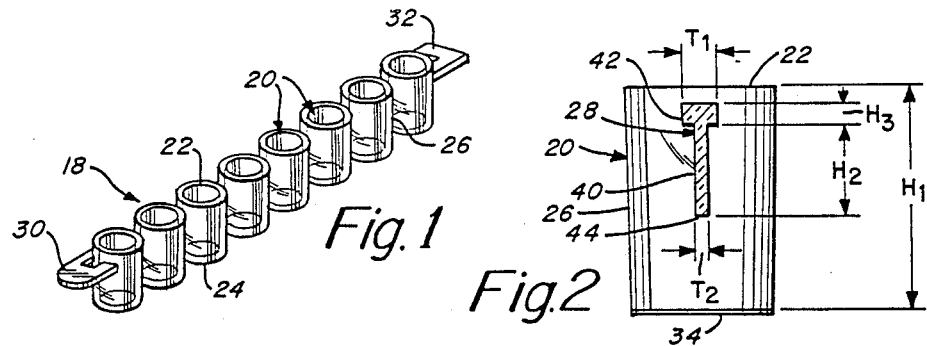
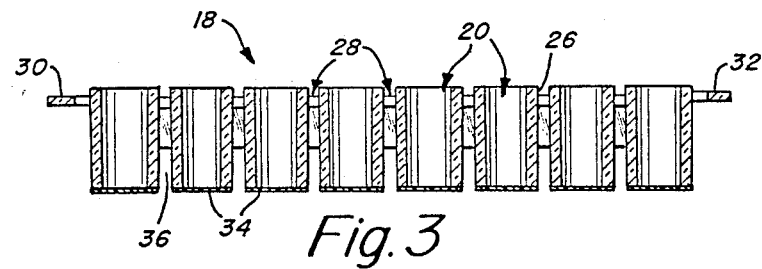
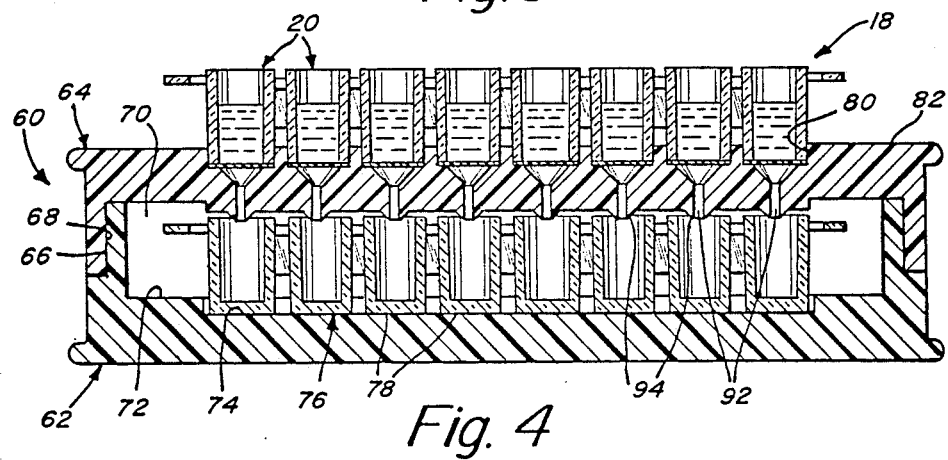
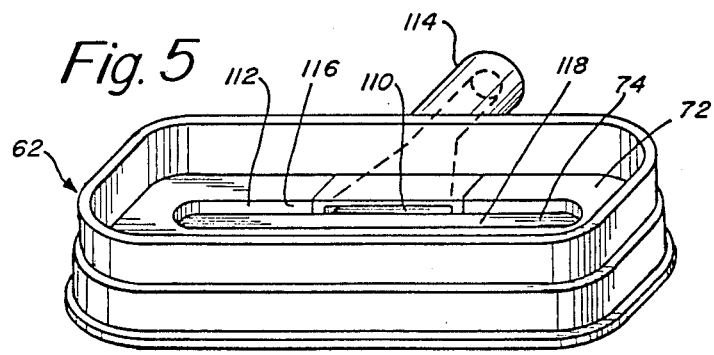

MULTI-WELL FILTER STRIP AND COMPOSITE ASSEMBLIES

RELATED APPLICATION

This application is a division of application Ser. No. 07/187,083, filed Apr. 28, 1988, now U.S. Pat. No. 4,895,706 which is a continuation-in-part of copending U.S. Ser. No. 923,906 filed Oct. 28, 1986, now abandoned, by Lyman et al., entitled MULTI-WELL TEST PLATE, which is hereby incorporated by reference.

BACKGROUND OF THE INVENTION

This invention concerns a multi-well filter strip useful in the assay of microliter quantities of a fluid.

Two basic analytical procedures utilizing microporous membrane filters are known. The first is simply the use of a microporous membrane to collect small particles for analysis, e.g., the collection of trichloroacetic protein precipatates on cellulose acetate membranes. The second is use of the filter in a more active sense wherein a first substance is immobilized in the filter and a reactant is applied to the filter for reacting with the substance, e.g., the immobilization of single strand RNA or DNA on a nitrocellulose membrane for use in nucleic acid hybridization. See Gillespie, D. and Spielgelman, S. Journal of Molecular Biology, 12: 829–842 (1965).

The scale of these analytical procedures continues to decrease such that a 96-well microplate utilizing test volumes of 100 to 200 microliters per well is now widely used. As the apparatus is miniaturized, it becomes more difficult to prevent cross-contamination of samples in adjacent wells and it becomes important to prevent any loss of the fluid from the small sample in the well during the reaction period. For example, U.S. Pat. No. 4,526,690 to Kiovsky et al. describes a 96-well apparatus utilizing test samples of 100 microliters and less. A complex filter structure is provided consisting of a continuous microporous membrane or ultrafiltration media 26 attached to the bottoms of the 96 wells, and to prevent contamination and dehydration, a hydrophobic fabric 30 is disposed below the membrane with a minute space 34 between the membrane and fabric and a guiding spike 60 is provided below each well. The hydrophobic fabric is said to prevent a loss of fluid by lateral migration and/or gravity flow from within the well in the absence of an applied differential pressure across the membrane. The spike is said to serve the dual functions of preventing loss of a pendant drop from the well during the reaction period and second as a guide by which fluids forming as a pendant drop are directed to the appropriate well chamber below.

Another multi-well test device is described in U.S. Pat. No. 4,407,943 to Cole et al. A molded plastic tray 12 has a detachable cover 18. The cover has a plurality of open-bottom cylindrical recesses 20 each having a membrane 22 heat-sealed to the lower rim of the recess. In use, a sample is poured into a recess and flows through the membrane into the tray. The membrane is washed and treated with reagents as needed to detect the presence or absence of a particular material in the sample (col. 9, line 63 to col. 10, line 13).

Another multi-well test device, described in U S. Pat. No. 4,246,339 to Cole et al., includes telescoping cover and base members 10, 12 defining a liquid reservoir therebetween, a resilient foam member 16 for biasing the members in an open position, a sorbent material 18 in the base member having a surface layer 36 and a bulk portion 38, and a plurality of wells 20 in the cover each of which has a bottom opening covered by a microporous membrane 22 sealed liquid-tight to the circumference of the opening. The sorbent material between the cover and base members is spaced from the membranes in the open position, but in contact therewith in the closed position. Liquids are passed from the wells through the membranes into the sorbent means by depressing the members to the closed position. The membranes may be washed to remove unreacted materials by relaxing the top member, placing wash liquid in the test wells, and again depressing the top member to pass the wash liquid through the membranes into the sorbent material. The upper surface layer of the sorbent material resists wetting by the liquid passing through the wells to minimize rewetting the membranes with previously-used liquids.

It is an object of this invention to provide a multi-well filter strip for use in a variety of filtering and assay procedures which minimizes contamination between adjacent wells and permits testing of very small microliter samples.

Another object is to provide a multi-well filter strip wherein the wells are removably attachable to a holder and to each other to permit selected testing of various wells.

Another object of the invention is to provide a multi-well filter strip wherein the contents of the wells are not contaminated by handling the strip and wherein radioactive or toxic specimens in the wells need not be contacted by the user.

Yet another object is to provide a multi-well filter assembly which can be used for prefiltration prior to the assay utilizing small sample volumes with good recovery.

A further object is to provide a multi-well filter strip for use in a vacuum manifold.

A still further object is to provide a vacuum manifold having means for positioning a filter strip and for directing filtrate which exits the filter strip.

A still further object is to provide a vacuum manifold having a structure for supporting the filter membranes to prevent separation of the membrane from the filter well while a differential pressure is applied across the membrane.

Yet another object is to provide a combination filter strip, transfer plate, and multi-well test plate wherein the transfer plate directs the filtrate passing through the membrane into a corresponding well of the test plate.

SUMMARY OF THE INVENTION

The invention is a multi-well filter strip and composite assemblies for filtering small quantities of liquid.

The filter strip consists of a plurality of cylindrical wells open at the top and bottom ends and arranged in a straight row and connected to one another by frangible webs which space the wells closely adjacent one another, but not touching, and discrete filter membranes closing the bottom end of each well with the filter membranes spaced from one another. The filter strip has outwardly extending tabs at each end for holding the strip and supporting the strip in a rectangular frame having an array of alpha-numeric designations for identifying each well supported by the holder. The strips are releasably attachable to the holder and the wells within each strip are releasably attached to permit separation of any number of wells in the strip.

A filter assembly includes a vacuum manifold having a base and removable cover, a chamber in the vacuum manifold, a passage in the manifold communicating with the chamber for applying a reduced pressure to the chamber, a multi-well filter strip, an array of cylindrical recesses in the cover for supporting the filter strip, and openings in the bottoms of the recesses for placing each membrane of the filter strip wells in communication with the chamber whereby a reduced pressure applied to the chamber will draw liquid in the wells through the membranes into the chamber. A closed bottom well strip may be positioned in a trough in the manifold base with each well of the array aligned below a well of the filter strip where it is desired to separately collect the filtrate passing through each membrane of the filter strip. A nozzle is provided around each opening in the cover for directing the filtrate from the membrane into an aligned closed bottom well for preventing spattering and cross contamination of the filtrate. The cylindrical recesses in the manifold cover for supporting each well of the filter strip each have a central funnel-shaped portion and a peripheral shoulder for supporting the periphery of the membrane and forming a seal at the bottom of the well. A vacuum control device is provided in the manifold cover for limiting the reduced pressure applied to the chamber. A fan-shaped passage is provided in the base of the manifold for removing the filtrate drawn into the chamber which is not contained within the closed well strip.

In another embodiment, a filter assembly is provided consisting of a multi-well filter strip, an array of closed bottom wells similar in size to the filter strip and disposed beneath the filter strip, and a transfer plate between the filter strip and closed bottom well array for engaging and aligning the same and causing the filtrate passing through each membrane of the filter strip to enter a corresponding separate well in the array. The transfer plate may be utilized in a pressure manifold for applying an increased pressure above the membranes of the filter strip to force liquid through the membranes.

BRIEF DESCRIPTION OF THE DRAWINGS

FIG. 1 is a perspective view of a filter strip constructed in accordance with this invention.

FIG. 2 is a side view of one well of the filter strip of FIG. 1, showing in cross-section the web which connects adjacent wells.

FIG. 3 is a cross-sectional view of the filter strip of FIG. 1.

FIG. 4 is a cross-sectional view of an assembly composed of a vacuum manifold having a base and cover, a closed well plate in the base, and a filter strip mounted on the manifold cover in accordance with this invention.

FIG. 5 is a top perspective view of the manifold base of FIG. 4.

DETAILED DESCRIPTION OF THE PREFERRED EMBODIMENTS

Figure 11:
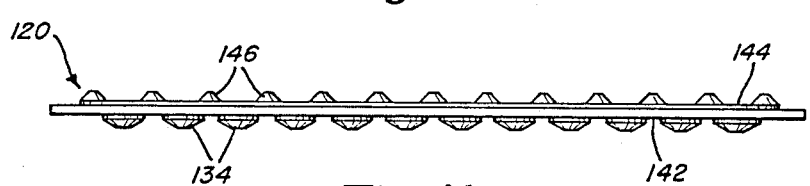
FIG. 11 is a side plan view of the transfer plate of FIG. 10.
Figure 12:
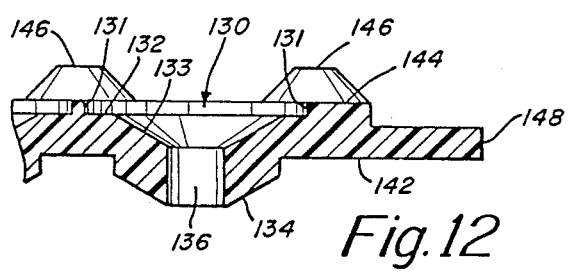
FIG. 12 is a fragmentary cross-sectional view of the transfer plate taken along section lines 12—12 in FIG. 10.
Figure 13:
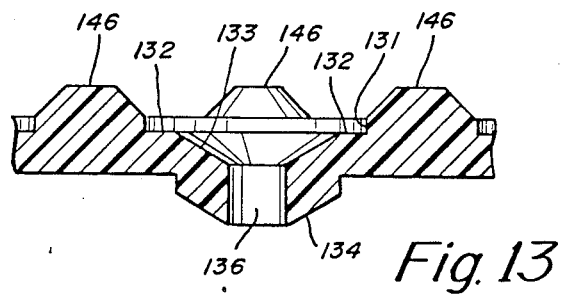
FIG. 13 is a fragmentary cross-sectional view of the transfer plate taken along section lines 13—13 in FIG. 10.

In FIGS. 1-3, a filter strip 18 of the present invention is shown composed of a row of eight generally cylindrical wells 20 each open at its top 22 and bottom 24 and having cylindrical side walls 26. The separate wells 20 are joined by frangible webs 28, and the strip is molded as a unitary structure of clear plastic. Rounded tab 30 and squared tab 32 at opposite ends of the strip are provided to identify each end of the strip and for handling and supporting the strip, either manually or in a frame-like support such as shown in FIG. 11 and in copending application Ser. No. 923,906, filed Oct. 28, 1986 by Lyman et al. and entitled MULTI-WELL TEST PLATE, which is hereby incorporated by reference.

The open bottom 24 of each well 20 is closed by a permeable membrane 34. The individual membranes for each well are discrete disks separate from the others so as to prevent any transfer of filtrate or retentate from the bottom of one well to another. It will also be noted that a gap 36 exists between the adjacent surfaces of adjacent wells so that no flow may occur on a well wall 26 from one to another of the wells. The membrane 34 which closes the bottom 24 of each well may be heat sealed, ultrasonically welded, or otherwise attached by solvent or adhesive to the bottom surface of the cylindrical wall 26.

The frangible webs 28 which join adjacent wells are shown in detail in FIG. 2. Each web includes an elongated main rib 40 which extends vertically between the wells and a transverse cross rib 42. The ribs 40 and 42 define a T-shaped cross-section for the webs 28. The height $H_2$ of main rib 40 is approximately one-half the height $H_1$ of the well 20, while the height $H_3$ of the transverse rib 42 is about one-quarter of the height $H_2$ (of main rib 40). The thickness $T_1$ of transverse rib 42 is greater than the thickness of $T_2$ of main rib 40. The specific dimensions of the web 28 may be those set forth in copending Ser. No. 923,906, or any other dimensions which hold the wells in a linear array and yet facilitate ready separation of the wells. Because the T-shaped webs which join adjacent wells have their lower edges 44 (bottom end of rib 40) disposed substantially above the bottoms 24 of the wells, a discrete gap exists between the wells which enables the wells to fit into separate receptacles provided for them in a vacuum manifold or a transfer plate with which they may be used, as described more fully below.

A well strip having the T-shaped webs described is easily and inexpensively molded as an integral body. The webs hold the wells in a flat linear array with all of the bottom surfaces of the wells in a single plane. The strip of wells may be easily removed from a support (see FIG. 9) by grasping one or both of the tabs 30 and 32 at the opposite ends of the strip, and when being handled, the strip will not curve or bend or sag unless intentional pressure for that purpose is applied to the strip. An individual well or a few wells may be broken from the strip 18 whenever it is necessary or desirable to use fewer than the full row.

In FIGS. 4-7, a vacuum manifold 60 with which the filter strip 18 may be used is shown. The vacuum manifold is an elongated housing composed of a base 62 and cover 64 that typically may be molded of polycarbonate material and having mating peripheral walls 66 and 68, respectively, that allow the cover to close tightly and form a seal on the base. The base and cover define a chamber 70 to which a reduced pressure may be applied as described below.

As shown in FIGS. 4 and 5 in the preferred form, the interior bottom wall 72 of base 62 is provided with a trough 74 into which a strip 76 of closed bottom wells 78 may fit and into which filtrate may be drawn when a reduced pressure is applied to chamber 70. The array 76 of closed bottom wells has essentially the same geometry as the filter strip 18 accepting only that the filter strip 18 has open bottom wells closed by the discrete membranes 34 while the closed bottom wells 78 are imperforate to any material. The array 18 may be identical to the multi-well strip shown in copending Ser. No. 923,906.

Cover 64 is provided with a row of cylindrical recesses 80 (FIG. 7) which receive the individual wells 20 of the filter strip 18. As is apparent in FIGS. 4, 6 and 7, the individual recesses 80 extending downwardly from the upper surface 82 of cover 64 are spaced apart by thin partitions 84 which separate the individual recesses from one another. Each recess has a bottom wall 86 having a funnel-shaped central portion 88 and surrounding shoulder 90. An opening 92 extends through the cover from the bottom of the funnel-shaped portion 88 so as to provide a through passage with the funnel for filtrate passing from a well 20 of the filter strip 18 into chamber 70. The shoulder 90 is dimensioned to engage the flat bottom 24 of the well 20 so as to support and seal the periphery of the filter membrane 34 which closes the bottom of the well.

It will be appreciated that when the filter strip is placed with its wells in the recesses 80 in the cover, liquid may be pulled from the wells of the filter strip through the membranes 34 when a pressure differential is applied across the membranes (i.e , by reducing the pressure in chamber 70). The filtrate pulled through the membranes may be either individually collected in the wells of the closed bottom well strip 76, or it may be mixed in the chamber 70. This latter arrangement would typically be used when the object is to collect the retentate in the filter strip wells rather than the filtrate from them. When the filtrate is the product to be derived from the procedure, obviously, separate wells 78 must be provided to collect the fluid separately from each of the filter strip wells 20.

The trough 74 formed in the base 62 of the vacuum manifold 60 serves to align the individual closed bottom wells 78 of the array 76 with the wells 20 in the filter strip 18. As is evident in FIG. 4, the opening 92 through the bottom wall 86 of each recess in the cover is aligned with the approximate center of the corresponding closed bottom well 78 when positioned in the trough 74 so that all of the filtrate is collected in the corresponding closed bottom well 78. To further assure discharge of the filtrate into the closed bottom wells, a downwardly extending flange 94 may be provided in the cover about each of the openings 92. Each flange 94 about its opening 92 defines a nozzle so as prevent the filtrate from spattering as it exits the passage 92 particularly if high vacuum (i.e., very low pressure) is applied to the chamber 70 causing high flow rates.

Figure 6:
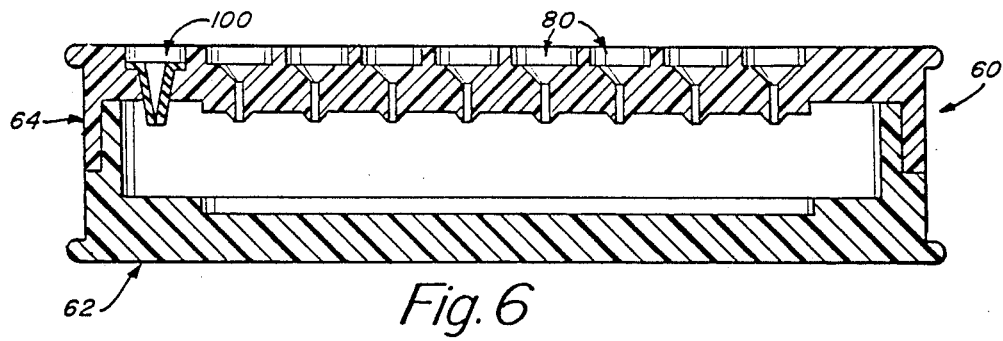
FIG. 6 is a cross-sectional view of a vacuum manifold similar to FIG. 4 but having a device for controlling the amount of vacuum.
Figure 7:
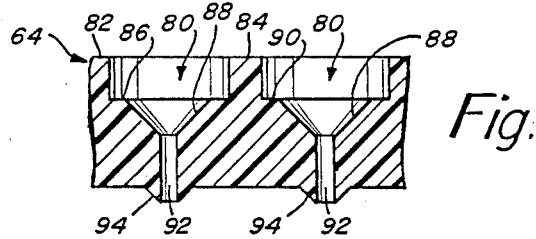
FIG. 7 is a fragmentary cross-sectional view of the well chambers in the manifold covers of FIGS. 4 and 6.

In FIG. 6, one of a variety of different devices which may be used to limit the vacuum applied to chamber 70 is shown incorporated into the vacuum manifold 60. In that figure, a duckbill valve 100 is shown formed in the cover 64 at one end of the row of wells 80. Alternatively, a ball check valve or any other well-known pressure relief device may be provided. Any of those arrangements will prevent excessive vacuums from being applied to the chamber 70, which would cause spattering or exceed the pressure which can be withstood by the membranes 34 that form the filter material across the bottoms of the wells 20. More preferably, the valve 100 is provided adjacent the passage 110 described below for even pressure control across the filter strip.

The means for applying a vacuum to the chamber 70 is shown in FIG. 5. A passage 110 extends through the side wall 112 of trough 74 and through a nipple 114 onto which tubing may be telescoped so as to connect the passage 110 to a vacuum pump (not shown). The opening 110 in this embodiment is shown to be generally fan-shaped, and its cross-sectional area diminishes smoothly from the inner surface 116 of trough side wall 112 to the extension of the passage 110 in nipple 114. The bottom of passage 110 in side wall 112 is at or below the level of the bottom wall 118 of the trough so that any liquid in the trough may be drawn by the vacuum out of the manifold through nipple 114. The fan-shaped arrangement of opening 110 disperses the airflow across substantially the entire bottom wall 118 of trough 74 so as to avoid spattering of any filtrate in the trough. It will be appreciated that if closed bottom wells are not provided in the trough, but rather the filtrate is permitted to collect in the trough itself, the configuration of the passage 110 will facilitate removal of all of that material. It is important that the passage 110 through which the vacuum is applied to the chamber 70 be in a position to remove all of the liquid which collects in the chamber.

Figure 8:
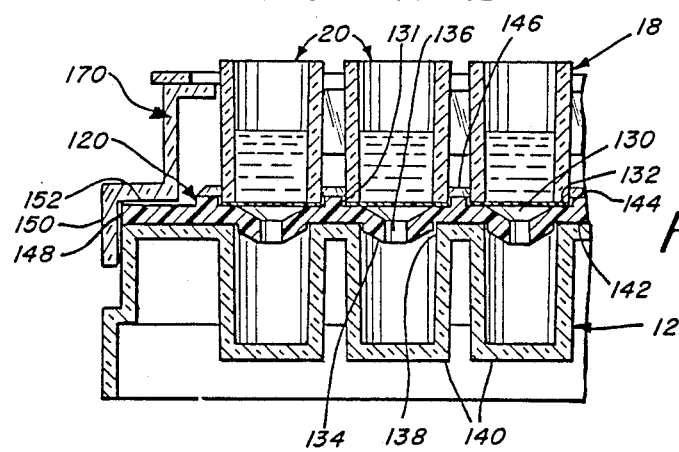
FIG. 8 is a fragmentary cross-sectional view of an assembly composed of a filter strip, strip holder, centrifugal transfer plate, and closed well plate in accordance with the present invention.
Figure 9:
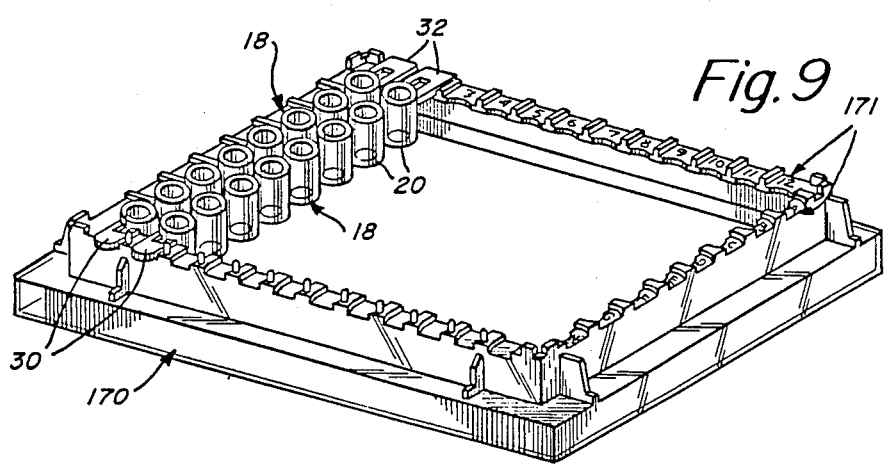
FIG. 9 is a top perspective view of a strip holder containing two filter strips as used in the assembly of FIG. 8.
Figure 10:
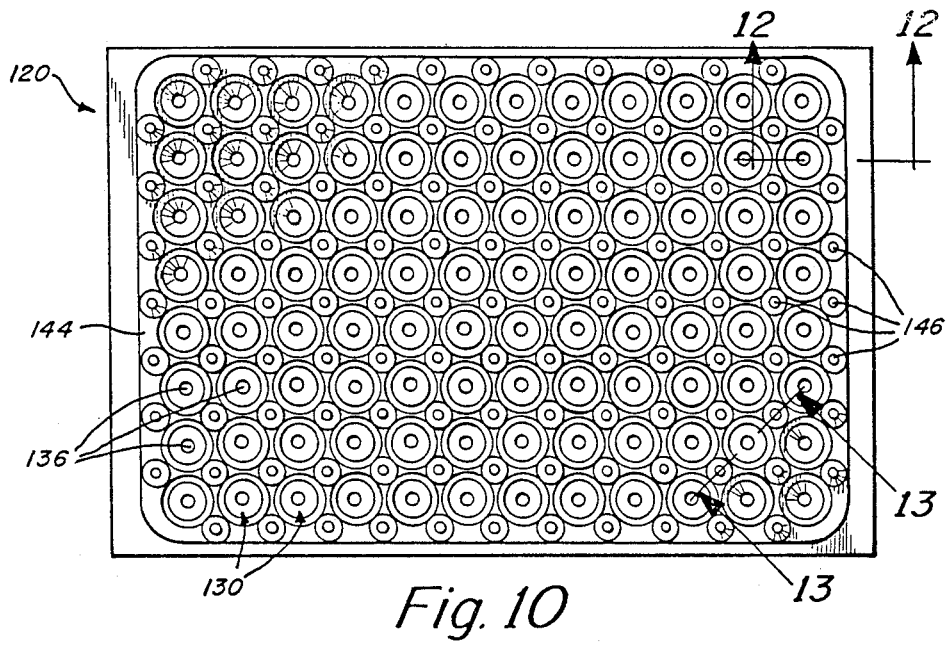
FIG. 10 is a top plan view of the centrifugal transfer plate as used in the assembly of FIG. 8.

In FIGS. 8-13, another assembly employing the filter strips is shown. In this assembly, shown in FIG. 8, a centrifugal transfer plate 120 places one or more filter strips 18 in communication with the closed bottom wells of a conventional 96-well plate 122 and transfer of the filtrate from the wells of strips 18 to the wells of plate 122 is induced by the action of a centrifuge (not shown). As shown in FIG. 9, a plurality of filter strips 18 are supported by a strip holder 170, which holder is described in detail in copending application Ser. No. 923,906. Holder 170 engages the peripheral edge of well plate 122 as described hereinafter. While a 96-well plate 122 is suggested, it should be appreciated that the plate may be replaced by a number of closed bottom strips identical to those shown in copending application Ser. No. 923,906, which may in turn be supported by a strip holder as shown in that application. The two holders for the filter strips and closed well strips may then register with one another in a manner similar to that shown in FIG. 8.

The transfer plate 120, shown separately in FIGS. 10-13, is a molded plastic piece having a number of cylindrical recesses 130 formed in its upper surface 144. Recesses 130 have vertical sidewalls 131 surrounding horizontal shoulders 132, which surround funnel-shaped bottom walls 133. Bottom walls 133 register with downwardly extending nozzles 134 having openings 136 therethrough. Each of the nozzles 134 has an outer diameter which enables it to register with the open top 138 of a well 140 in the 96-well plate 122 (see FIG. 8). The fit of the nozzle 134 in the open well 140 is such that a slight clearance is provided through which any build up of gas in the well 140 may be vented. The nozzles 134 extend downwardly from the lower surface 142 of the transfer plate so as to enter into the closed bottom wells 140 and prevent cross contamination of filtrate from one well to another in plate 122.

The vertical walls 131 of recesses 130 engage the outer sidewalls of wells 20 of filter strip 18 while the horizontal shoulders 132 engage the flat bottom surfaces 24 of wells 20 of the filter strip 18. The shoulders 132 serve to align the wells 20 with the openings 136 through the transfer plate 120, and also serve to support the periphery of the filter membranes 34 so as to prevent the membranes from peeling off the bottoms of the wells 120 when high pressure differentials are applied to the membranes.

To further assist in aligning the filter strips with the transfer plate 120, tapered posts 146 are provided on the upper surface 144 of the transfer plate in the space defined by four adjacent funnel-shaped recesses. The tapered configuration of the post 146 will guide the lower outside edges of wells 20 into position between recess sidewalls 131 (which may be tapered) and onto the flat shoulders 132 as shown in FIG. 8.

To further assist in aligning the assembly of FIG. 8, peripheral edge 148 of the transfer plate 120 may just fit within a vertical flange 150 at the lower edge of the strip holder 170. A horizontal shoulder 152 adjacent flange 150 of the holder 170 may engage the upper surface 144 of the transfer plate so as to support the transfer plate at the proper height so as to just engage the bottom 24 of each well 20.

It will be appreciated that because the assembly is subjected to centrifugal force, no seals are required to maintain vacuums as in the embodiment of FIGS. 4-7, and the same driving force is applied to the liquid in each of the wells to cause the liquid to flow through the membranes 34 and collect in the 96-well plate or closed bottom well strips attached to the bottom surface of the transfer plate for that purpose.

Figure 14:
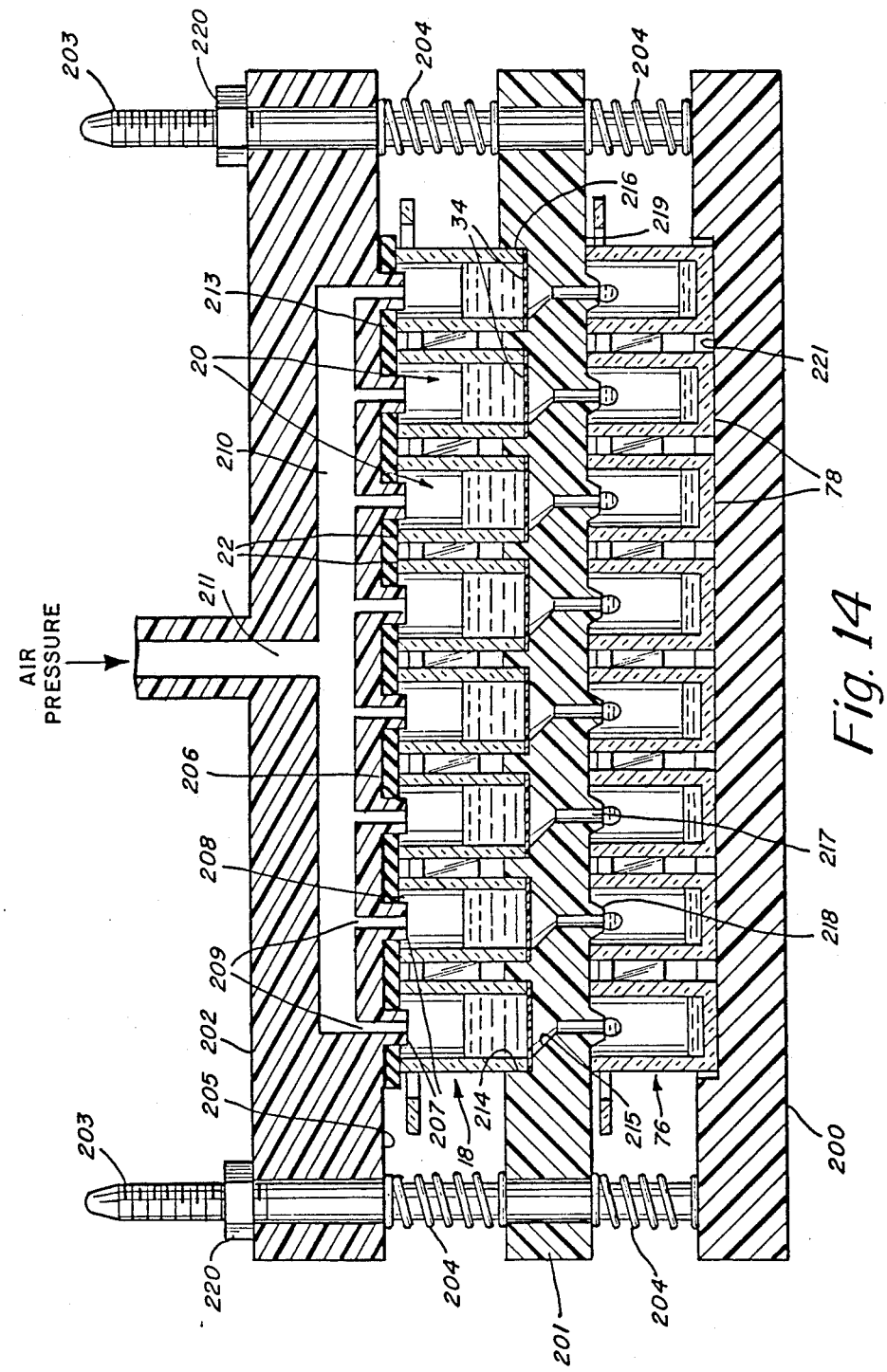
FIG. 14 is a cross-sectional view of an assembly composed of a pressure manifold, a rubber gasket, a filter strip, a transfer plate and a closed well plate, in accordance with the present invention.
Figure 15:
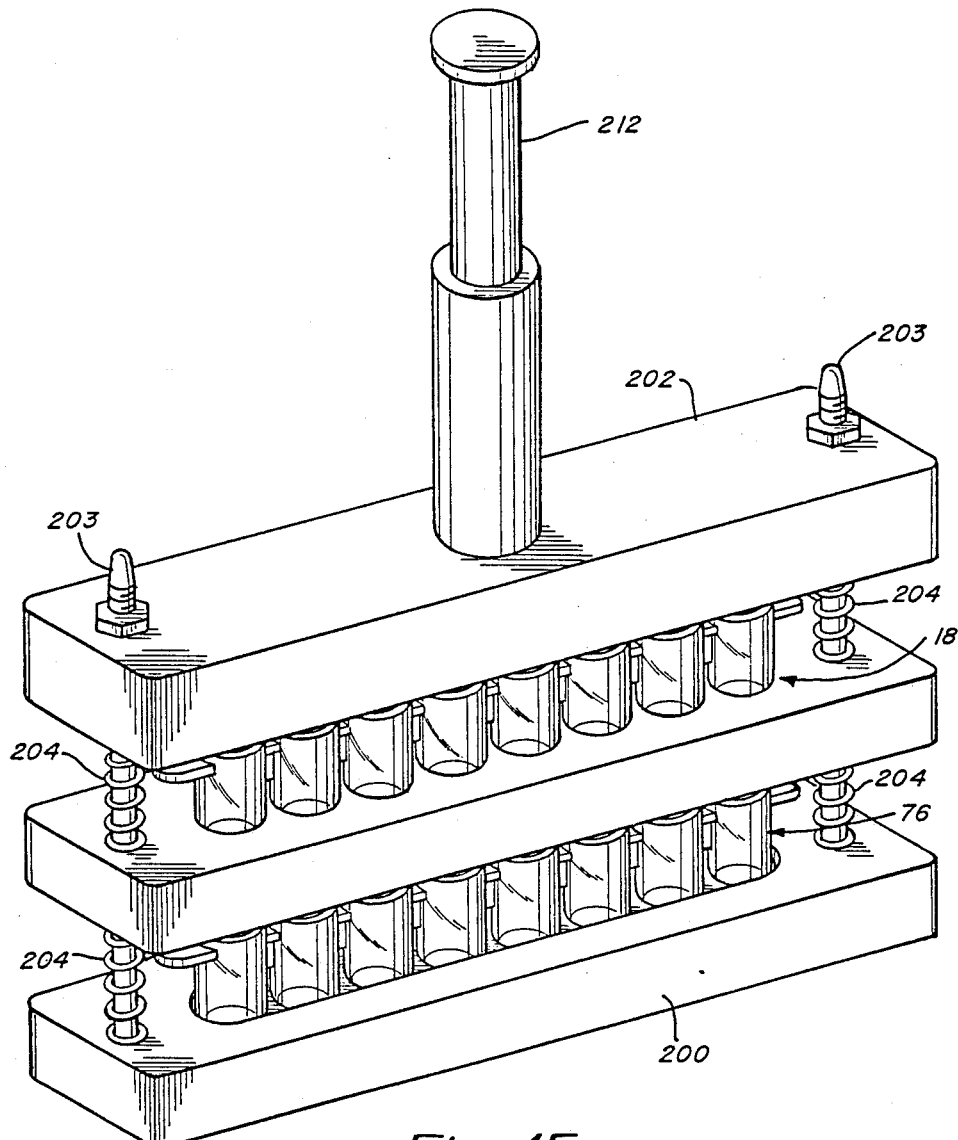
FIG. 15 is a top perspective view of a syringe and the assembly of FIG. 14 with the components spread apart for loading or unloading of the filter strip and closed well plate into the pressure manifold.

FIGS. 14-15 show yet another embodiment of the invention wherein a pressure manifold contains an 8-well filter strip and an 8-well closed bottom strip. The pressure manifold consists of a base 200, transfer plate 201, and cover 202 stacked in vertical relationship and releasably attached by a pair of outer vertical posts 203 which pass through aligned bores in the base, transfer plate, and cover. Springs 204 are provided around the posts between each of the base, transfer plate, and cover for biasing the components away from one another to facilitate loading and unloading of the filter strip 18 and closed bottom well strip 76 above and below the transfer plate respectively as shown in FIG. 15. Releasable clamping means such as bolts 220 are provided which act against the spring bias to hold the components in a closed position during filtering, as shown in FIG. 14.

The lower surface of manifold cover 202 has an indented shoulder 205 at each end and a protruding central portion 206 in which there is formed a straight row of eight nozzles 207 and between the nozzles a row of recesses 208. Each nozzle 207 has a central opening 209 which is connected to a horizontal chamber 210 extending lengthwise in the cover interior and which is connected to a central bore 211. An air pressure device such as syringe 212 is releasably connected to bore 211 for applying an increased pressure via chamber 210 and nozzle openings 209 to each of the wells 20 of the filter strip 18 disposed between the transfer plate and cover. A rubber gasket 213 forms a compliant seal between each of recesses 208 and the upper ends 22 of wells 20 for sealing the filter strip against the cover. Thus, in contrast to the vacuum manifold of FIGS. 4-7 wherein a reduced pressure is applied below the membranes 34 of the filter strip, in the pressure system of FIGS. 14-15 an increased pressure is applied above the membranes 34 to force the samples in wells 20 through the membranes 34.

The transfer plate 201 is configured in substantially the same manner as the transfer plate 120 in FIGS. 10-13, wherein upper cylindrical recesses 214 have funnel-shaped bottom walls 215 and outer shoulders 216 for supporting the bottoms of wells 20 and central openings 217 through nozzles 218 for directing the filtrate into an aligned well 78 below the transfer plate. The lower surface 219 of transfer plate 201 rests upon the upper surface of the well strip 76. A trough 221 is provided in the upper surface of base 200 for supporting and aligning the well strip 76 beneath the transfer plate 201.

Having described this invention in detail, the many advantages of the present invention will be fully appreciated. The configuration of filter strip 18 allows multiple filtering of small volumes and provides easy handling. The frangible webs 28 which connect adjacent filter wells 20 allow individual filter strips 18 to be broken apart into separate wells. Typically, this may be advantageous when it is desired to place the filtered retentate into a vial for testing.

As yet another advantage of this invention, the filter assemblies provide for filtering of up to 96 samples simultaneously without losing the matrix location of each well. This is achieved by using the holder of FIG. 9 with twelve filter strips. The special orientation of the strips 18 is imposed by the end tabs 30 and 32 and the alpha-numeric designations 171 on the holder 170 as described in detail in copending application Ser. No. 923,906. This is particularly important when the device is used in diagnostic applications where each well or strip may be from a different patient, or in any other application where multiple samples are to be processed.

Furthermore, this invention enables the membranes to be handled on an individual well or strip basis which provides significant convenience for the user. Waste is reduced by enabling the user to select only the number of strips required.

It will also be appreciated that a filter as a substrate base is very desirable in many analytical diagnostic applications where the test being performed relies upon the physical or chemical binding of the test sample to the internal and external surfaces of the substrate. A microporous membrane has a vastly greater surface area than a nonporous flat surface, and therefore a very substantial increase in binding occurs. Furthermore, many specialized membrane materials, including ultrafiltration media, are available to achieve specific binding properties (as used herein, filter membrane includes ultrafiltration media). It will also be appreciated that after the binding steps are complete, most diagnostic tests require a series of reaction and washing steps to flush away the unreacted or unbound material. The use of an eight-well strip with either a vacuum manifold or centrifugal transfer plate enhances the ease with which the reaction and washing steps may occur.

As a further advantage of this invention, during an incubation period the well tops of the filter strip can be sealed with a plate or stopper (e.g., a pressure sensitive film) and the filter strip placed over a closed bottom strip in which water has been added to maintain the humidity and prevent dehydration. The lower strip also prevents the contents of the filter strip from dripping onto the workbench.

Having described this invention in detail, those skilled in the art will appreciate that numerous modifications may be made thereof without departing from its spirit. Therefore, the breadth of this invention is not to be limited to the specific embodiments illustrated and described. Rather, its breadth is to be determined by the appended claims and their equivalents.

What is claimed is:

1. A filter assembly comprising
   a multi-well filter strip having a plurality of wells, each of the wells having side walls and open top and bottom ends,
   each of the wells further having a separate filter membrane attached to a bottom surface of the side walls and closing the open bottom end of each well of the strip,
   an array of wells having open top and closed bottom ends and being spaced so that the array of closed bottom wells will align with the wells of the filter strip, and
   a transfer plate having means for supporting each membrane adjacent the bottom ends of the respective wells in the filter strip and for engaging each of the wells in the array adjacent the open top end thereof for causing filtrate passing through the membranes on the wells in the filter strip to enter the corresponding separate wells in the array of wells aligned therewith.

2. A filter assembly as defined in claim 1 wherein
   the supporting means comprises a plurality of individual recesses each receiving the bottom end of a respective well of the filter strip, each recess having a bottom wall with a peripheral shoulder portion for supporting the respective membrane, and
   means defining openings extending through each of the bottom walls in the recesses to pass filtrate through the transfer plate.

3. A filter assembly as defined in claim 2 wherein
   the supporting means includes nozzle means extending downwardly from each opening for registering the wells of the array with the wells of the strip and preventing the intermixing of filtrate passing from each well of the filter strip through the respective membrane to a well of the array.

4. A filter assembly as defined in claim 1 further comprising
   a pressure manifold including a base and cover wherein the filter strip, transfer plate and closed bottom array of wells are disposed between the cover and base.

5. A filter assembly comprising:
   a multi-well filter strip having a plurality of wells, each of the wells having side walls and open top and bottom ends, each of the wells further having a separate filter membrane attached to a bottom surface of the side walls and closing the open bottom end of each well of the strip,
   a transfer plate having means for supporting each membrane adjacent the bottom ends of the respective wells; and
   means defining openings in the transfer plate adjacent each membrane, wherein by applying a reduced pressure beneath the membrane to draw liquid in the wells through the membranes the supporting means maintains the membrane attachment to the well.

6. The filter assembly of claim 5, wherein
   the supporting means comprises a plurality of individual recesses each receiving a bottom end of a respective well of the filter strip, each recess having a bottom wall with a peripheral shoulder portion for supporting the respective membrane, and
   said openings extend from each recess.

7. The filter assembly of claim 6, wherein
   the bottom wall of each recess has a central funnel-shaped portion which is surrounded by the shoulder portion.
   the shoulder portion of each recess forming a seal with the bottom end of each respective well.

8. The filter assembly of claim 5, wherein
   the supporting means provided on the transfer plate includes nozzle means extending downwardly from each opening which prevents the intermixing of filtrate passing from each well through the respective membrane.

9. The filter assembly as defined in claim 5, wherein
   frangible webs connect the separate wells of the filter strip enabling the wells to be easily separated from one another.

* * * * *

UNITED STATES PATENT AND TRADEMARK OFFICE
CERTIFICATE OF CORRECTION

PATENT NO. : 4,948,564

DATED : August 14, 1990

INVENTOR(S) : Root et al

It is certified that error appears in the above-identified patent and that said Letters Patent is hereby corrected as shown below:

Column 1, line 27, after "S." insert a --,-- (comma)

Column 9, line 54, delete "therewith" and substitute therefore --with them--.

Column 10, line 3, delete "means defining".

Signed and Sealed this

Twenty-fourth Day of December, 1991

Attest:

HARRY F. MANBECK, JR.

*Attesting Officer*    *Commissioner of Patents and Trademarks*